United States Patent [19]

Kloss et al.

[11] 4,220,756
[45] Sep. 2, 1980

[54] METHOD OF PRODUCING 3-O-DEMETHYLFORTIMICIN B,4-N-ALKYLFORTIMICIN B DERIVATIVES AND RELATED AMINOGLYCOSIDE ANTIBIOTICS

[75] Inventors: John Kloss; Alex M. Nadzan, both of Gurnee, Ill.

[73] Assignee: Abbott Laboratories, North Chicago, Ill.

[21] Appl. No.: 25,239

[22] Filed: Mar. 29, 1979

[51] Int. Cl.² .......................... A61K 71/31; C07H 15/22
[52] U.S. Cl. .................................. 536/17 R; 424/180; 536/18
[58] Field of Search .............................. 536/17 R, 120

[56] References Cited

U.S. PATENT DOCUMENTS 4,124,756 11/1978 Martin et al. .......................... 536/17

*Primary Examiner*—Johnnie R. Brown
*Attorney, Agent, or Firm*—Robert L. Niblack; Gildo E. Fato; Joyce R. Niblack

[57] ABSTRACT

An improved method of 3-O-demethylating fortimicin B or a 4-N-alkylfortimicin B derivative comprising the steps of reacting fortimicin B with lithium in the presence of ethylenediamine and thereafter isolating 3-O-demethylfortimicin B from the reaction mixture.

6 Claims, No Drawings

METHOD OF PRODUCING 3-O-DEMETHYLFORTIMICIN B,4-N-ALKYLFORTIMICIN B DERIVATIVES AND RELATED AMINOGLYCOSIDE ANTIBIOTICS

BACKGROUND OF THE INVENTION

The aminoglycoside antibiotics are a valuable therapeutic class of antibiotics which include the kanamycins, gentamicins, streptomycins and the more recently discovered fortimicins. While the naturally produced parent antibiotics are valuable broad spectrum antibiotics, it has been found that chemical modification of the parent structures improve the activity in one of several ways, either by improving the intrinsic activity, improving the activity against resistant strains or reducing the toxicity of the parent antibiotics. Further, because of the development of aminoglycoside-resistant strains and inactivation of the parent antibiotics by R-mediated factors which can develop, the search for new entities continues.

One valuable class of fortimicin antibiotics, the 3-O-demethylfortimicins, are disclosed in U.S. Pat. No. 4,124,756, issued Nov. 7, 1978. Of particular interest is 3-O-demethylfortimicin A. 3-O-demethylfortimicin B is equally of interest as an intermediate for synthesizing the 4-N-acyl and alkyl derivatives of 3-O-demethylfortimicin A.

In the previously described method for producing 3-O-demethylfortimicin B, fortimicin B was demethylated using lithium wire in ethylamine. Surprisingly, it has now been found that the yield can be increased to over fifty percent by employing ethylenediamine rather than ethylamine as the solvent.

SUMMARY OF THE INVENTION

The present invention provides an improved process for producing 3-O-demethylfortimicin B or a 4-N-alkylfortimicin B derivative comprising the steps of 3-O-demethylating fortimicin B with lithium in the presence of ethylenediamine, removal of the excess lithium and solvent, and isolation of 3-O-demethylfortimicin B by chromatography.

DETAILED DESCRIPTION OF PREFERRED EMBODIMENTS

Generally speaking, the process of this invention comprises the steps of adding from 0.1 g to 16 g of lithium wire to each 100 ml of ethylenediamine which has been distilled from sodium and stirring the mixture under a nitrogen atmosphere at a temperature of from about 8° to about 116°C. for from about 1 to about 30 minutes until a deep blue color appears. Thereafter, from 0.35 g to about 20 g of fortimicin B per 100 ml of ethylenediamine is added and the reaction mixture stirred, preferably at ambient temperature, until the lithium is depleted (the blue color disappears). A second addition of from about 0.1 to about 16 g of lithium is made and the reaction continued for from about 1 to about 3 hours until the second portion of lithium is exhausted and thereafter adding a third portion of from about 0.1 g to about 16 g of lithium wire and continuing the reaction for another 1 to 5 hours. The reaction mixture is then quenched carefully with, for example, methanol after the characteristic blue color disappears. Removal of the solvents in vacuo affords a residue which is passed through a short column (20 to 500 cm) packed with a suitable material such as silica gel, Sephadex, etc. and purification of the active fractions by column chromatography using suitable solvent systems such as chloroform-methanol-concentrated ammonia or systems of similar polarity such as methylene chloride-methanol-concentrated ammonia, etc., or some other suitable proton source such as ammonium chloride, ammonium phosphate, phosphoric acid and related phosphate salts, yields the desired 3-O-demethylated fortimicin B in a yield of about fifty-four percent. The use of such salts eliminates the step of passing the residue through a desalting column. However, when methanol is used, the residue is treated as described below. In the practice of the invention, it is preferred but not necessary to add lithium in stepwise portions to reduce the likelihood of side reactions.

Fortimicin B can be prepared according to the process described in U.S. Pat. No. 3,931,400.

Ethylenediamine can be purchased from Aldrich Chemical Co., Milwaukee, Wisconsin. Lithium wire can be obtained from Alfa Inorganics. Phosphorus pentoxide is available from Mallincrodt Chemical Co. Silica gel can be purchased from E. Merck & Co., and methanol, chloroform and ammonia are all available from Mallincrodt Chemical Co.

The following example further illustrates the present invention.

Example

Preparation of 3-O-Demethylfortimicin B

Lithium wire (1.59 g, 230 mmole, 12.5 cm) was added as freshly cut 5 mm pieces to 100 ml of ethylenediamine (distilled from sodium) contained in a 500 ml reaction flask equipped with an overhead mechanical stirrer and under a nitrogen atmosphere. After the appearance of a deep blue color (about 5 minutes), fortimicin B (2.0 g, 5.7 mmole, dried in vacuo over phosphorus pentoxide) was introduced and the reaction mixture stirred at ambient temperature until the lithium was depleted (30 minutes) at which time, a second addition of lithium (12.5 cm) was made. The reaction was continued for 1 hour and then a final portion of lithium wire (12.5 cm) was introduced and the reaction continued for another 3 hours. After the characteristic blue color disappeared, the reaction mixture was carefully quenched with methanol (300 ml). Removal of the methanol and ethylendiamine under high vacuum afforded a residue which was passed through a column of silica gel (1.5×45 cm ) using chloroform-methanol-concentrated ammonia (1:2:1 v/v/v) to remove the bulk of salts. Concentration of the appropriate fraction resulted in crude product which was purified by column chromatography over silica gel using chloroform-2-propanol-concentrated ammonia (2:4:1 v/v/v). Removal of solvent from the appropriate fractions yielded 1.0 g (3.1 mmole, 54%) of the desired 3-O-demethylfortimicin B: $^1$H NMR (D$_2$O) δ 1.11 (d, J=7 Hz, C$_6'$—CH$_3$), 1.40-2.03 (m, C$_3'$H$_2$—C$_4'$H$_2$), 2.44 (s,N—CH$_3$), 5.13 (d, J=4 Hz); $^{13}$C NMR (D$_2$O) δ 18.05, 26.77, 27.30, 35.50, 50.33, 50.84, 53.36, 64.71, 69.57, 71.13, 71.60, 74.36, 83.70, 102.06.

It will be understood by those skilled in the art that this method can be employed to 3-O-demethylate any other fortimicin and related aminoglycoside antibiotics which does not contain a 4-N-acyl group which would be cleaved under the reaction conditions of this invention.

We claim:

1. A process of preparing 3-O-demethylfortimicin B or a 4-N-alkyl derivative thereof comprising the steps of reacting a fortimicin to be O-demethylated with a first portion of lithium in the presense of ethylenediamine, said lithium and ethylenediamine having first been reacted under an inert atmosphere at a temperature of between 8° and 116° C., inclusive, until a blue color appears, said fortimicin and said lithium solution being stirred at ambient temperature until said blue color disappears, and thereafter isolating the 3-O-demethylfortimicin from the reaction mixture.

2. The method of claim 1 wherein said lithium is lithium wire.

3. The method of claim 1 wherein said 3-O-demethylated fortimicin is recovered by column chromatography.

4. The method of claim 1 wherein said fortimicin is treated stepwise with lithium wire in ethylenediamine.

5. A process of O-demethylating an aminoglycoside antibiotic which does not contain an acyl group which could be cleaved during demethylation, comprising the steps of reacting a first portion of lithium with ethylenediamine in an inert atmosphere at a temperature of between 8° and 116° C., inclusive, until a deep blue color appears, adding the aminoglycoside antibiotic to be O-demethylated to said reaction mixture and reacting said antibiotic with said lithium until said lithium is depleted and the blue color disappears, and recovering the demethylated antibiotic from the reaction mixture.

6. The method of claim 5 comprising the steps of:
(a) adding a first portion of from 0.1 to 16 g of lithium to each 100 ml of ethylenediamine;
(b) stirring said mixture under a nitrogen atmosphere at a temperature of from 8° to 116° C. until a deep blue color appears;
(c) adding from 0.35 to 20 g of antibiotic to each 100 ml of ethylenediamine and reacting said antibiotic with said lithium until the blue color disappears;
(d) adding a second portion of from 0.1 to 16 g of lithium to said reaction mixture and continuing said reaction until said lithium is depleted;
(e) and therefore recovering said O-demthylated antibiotic from the reaction mixture.

* * * * *